(12) United States Patent
Baumeister et al.

(10) Patent No.: US 12,144,633 B2
(45) Date of Patent: Nov. 19, 2024

(54) METHOD AND DEVICE FOR CARDIAC MONITORING

(71) Applicant: Cardisio GmbH, Frankfurt am Main (DE)

(72) Inventors: Meik Baumeister, Breisach (DE); Gero Tenderich, Toenisvorst (DE)

(73) Assignee: Cardisio GmbH, Frankfurt Am Main (DE)

( * ) Notice: Subject to any disclaimer, the term of this patent is extended or adjusted under 35 U.S.C. 154(b) by 612 days.

(21) Appl. No.: 17/197,988

(22) Filed: Mar. 10, 2021

(65) Prior Publication Data

US 2021/0204857 A1 Jul. 8, 2021

Related U.S. Application Data

(63) Continuation of application No. PCT/DE2019/100808, filed on Sep. 10, 2019.

(30) Foreign Application Priority Data

Sep. 10, 2018 (DE) ...................... 10 2018 121 974.1

(51) Int. Cl.
| | |
|---|---|
| *A61B 5/341* | (2021.01) |
| *A61B 5/00* | (2006.01) |
| *A61B 5/271* | (2021.01) |
| *A61B 5/352* | (2021.01) |
| *A61B 5/355* | (2021.01) |

(Continued)

(52) U.S. Cl.
CPC .............. *A61B 5/341* (2021.01); *A61B 5/271* (2021.01); *A61B 5/352* (2021.01); *A61B 5/355* (2021.01); *A61B 5/725* (2013.01); *G16H 50/20* (2018.01); *G16H 50/30* (2018.01); *G16H 50/70* (2018.01); *A61B 2560/02* (2013.01)

(58) Field of Classification Search
CPC ..... A61B 2560/02; A61B 5/271; A61B 5/341; A61B 5/352; A61B 5/355; A61B 5/725; G16H 50/20; G16H 50/30; G16H 50/70
See application file for complete search history.

(56) References Cited

U.S. PATENT DOCUMENTS

| | | |
|---|---|---|
| 4,569,357 A | 2/1986 | Sanz et al. |
| 2015/0201856 A1 | 7/2015 | Stork et al. |

FOREIGN PATENT DOCUMENTS

| | | |
|---|---|---|
| CN | 108420454 A | 8/2018 |
| DE | 10 2012 106 893 A1 | 2/2014 |

(Continued)

*Primary Examiner* — Amanda K Hulbert
(74) *Attorney, Agent, or Firm* — Muncy, Geissler, Olds & Lowe, P.C.

(57) ABSTRACT

A method for early identification of the presence of coronary heart disease or an arrhythmia in a patient being examined, including the steps of: (i) non-invasive recording of EKG signals at the patient's heart when resting, (ii) filter processing of the recorded EKG signals, (iii) transferring the filtered EKG signals into orthogonalised measurement variables on the basis of vectorcardiography, and (iv) entering the orthogonalised and, in the case of incorrectly applied electrodes, corrected measurement variables into a system based on artificial intelligence in which known findings data from comparative patients are stored and, by comparing these entered orthogonalised measurement variables with the findings data of the comparative patients within the AI system, a diagnosis is obtained for the patient being examined.

10 Claims, 18 Drawing Sheets

(51) Int. Cl.
    *G16H 50/20*     (2018.01)
    *G16H 50/30*     (2018.01)
    *G16H 50/70*     (2018.01)

(56)     References Cited

FOREIGN PATENT DOCUMENTS

| | | |
|---|---|---|
| EP | 0 086 429 A2 | 8/1983 |
| JP | 2008-220556 A | 9/2008 |
| WO | WO 03/057031 A1 | 7/2003 |

1. Mag-Difference-QRS_begin-R
2. Mag-Difference-QRS_begin-QRS_end
3. Mag-Difference-QRS_begin-T_begin
4. Mag-Difference-QRS_begin-T
5. Mag-Difference-QRS_begin-T_end
6. Mag-Difference-R-QRS_end
7. Mag-Difference-R-T_begin
8. Mag-Difference-R-T
9. Mag-Difference-R-T_end
10. Mag-Difference-QRS_end-T_begin
11. Mag-Difference-QRS_end-T
12. Mag-Difference-QRS_end-T_end
13. Mag-Difference-T_begin-T
14. Mag-Difference-T_begin-T_end
15. Mag-Difference-T-T_end
16. Azi-Difference-QRS_begin-R
17. Azi-Difference-QRS_begin-QRS_end
18. Azi-Difference-QRS_begin-T_begin
19. Azi-Difference-QRS_begin-T
20. Azi-Difference-QRS_begin-T_end
21. Azi-Difference-R-QRS_end
22. Azi-Difference-R-T_begin
23. Azi-Difference-R-T
24. Azi-Difference-R-T_end
25. Azi-Difference-QRS_end-T_begin
26. Azi-Difference-QRS_end-T
27. Azi-Difference-QRS_end-T_end
28. Azi-Difference-T_begin-T
29. Azi-Difference-T_begin-T_end
30. Azi-Difference-T-T_end
31. Ele-Difference-QRS_begin-R
32. Ele-Difference-QRS_begin-QRS_end
33. Ele-Difference-QRS_begin-T_begin
34. Ele-Difference-QRS_begin-T
35. Ele-Difference-QRS_begin-T_end
36. Ele-Difference-R-QRS_end
37. Ele-Difference-R-T_begin
38. Ele-Difference-R-T
39. Ele-Difference-R-T_end
40. Ele-Difference-QRS_end-T_begin
41. Ele-Difference-QRS_end-T
42. Ele-Difference-QRS_end-T_end
43. Ele-Difference-T_begin-T
44. Ele-Difference-T_begin-T_end
45. Ele-Difference-T-T_end
46. Mag-Triangle-QRS_begin-R-QRS_end
47. Mag-Triangle-QRS_begin-R-T_begin
48. Mag-Triangle-QRS_begin-R-T
49. Mag-Triangle-QRS_begin-R-T_end
50. Mag-Triangle-QRS_begin-QRS_end-T_begin
51. Mag-Triangle-QRS_begin-QRS_end-T
52. Mag-Triangle-QRS_begin-QRS_end-T_end
53. Mag-Triangle-QRS_begin-T_begin-T
54. Mag-Triangle-QRS_begin-T_begin-T_end
55. Mag-Triangle-QRS_begin-T-T_end
56. Mag-Triangle-R-QRS_end-T_begin
57. Mag-Triangle-R-QRS_end-T
58. Mag-Triangle-R-QRS_end-T_end
59. Mag-Triangle-R-T_begin-T
60. Mag-Triangle-R-T_begin-T_end
61. Mag-Triangle-R-T-T_end
62. Mag-Triangle-QRS_end-T_begin-T
63. Mag-Triangle-QRS_end-T_begin-T_end
64. Mag-Triangle-QRS_end-T-T_end
65. Mag-Triangle-T_begin-T-T_end
66. Cartesian-TimeDiff-QRS_beginX-QRS_beginY
67. Cartesian-TimeDiff-QRS_beginX-QRS_beginZ
68. Cartesian-TimeDiff-QRS_beginX-RX
69. Cartesian-TimeDiff-QRS_beginX-RY
70. Cartesian-TimeDiff-QRS_beginX-RZ
71. Cartesian-TimeDiff-QRS_beginX-QRS_endX
72. Cartesian-TimeDiff-QRS_beginX-QRS_endY
73. Cartesian-TimeDiff-QRS_beginX-QRS_endZ
74. Cartesian-TimeDiff-QRS_beginX-T_beginX
75. Cartesian-TimeDiff-QRS_beginX-T_beginY
76. Cartesian-TimeDiff-QRS_beginX-T_beginZ
77. Cartesian-TimeDiff-QRS_beginX-TX
78. Cartesian-TimeDiff-QRS_beginX-TY
79. Cartesian-TimeDiff-QRS_beginX-TZ
80. Cartesian-TimeDiff-QRS_beginX-T_endX
81. Cartesian-TimeDiff-QRS_beginX-T_endY
82. Cartesian-TimeDiff-QRS_beginX-T_endZ
83. Cartesian-TimeDiff-QRS_beginY-QRS_beginZ
84. Cartesian-TimeDiff-QRS_beginY-RX
85. Cartesian-TimeDiff-QRS_beginY-RY
86. Cartesian-TimeDiff-QRS_beginY-RZ

Fig. 11A

87. Cartesian-TimeDiff-QRS_beginY-QRS_endX
88. Cartesian-TimeDiff-QRS_beginY-QRS_endY
89. Cartesian-TimeDiff-QRS_beginY-QRS_endZ
90. Cartesian-TimeDiff-QRS_beginY-T_beginX
91. Cartesian-TimeDiff-QRS_beginY-T_beginY
92. Cartesian-TimeDiff-QRS_beginY-T_beginZ
93. Cartesian-TimeDiff-QRS_beginY-TX
94. Cartesian-TimeDiff-QRS_beginY-TY
95. Cartesian-TimeDiff-QRS_beginY-TZ
96. Cartesian-TimeDiff-QRS_beginY-T_endX
97. Cartesian-TimeDiff-QRS_beginY-T_endY
98. Cartesian-TimeDiff-QRS_beginY-T_endZ
99. Cartesian-TimeDiff-QRS_beginZ-RX
100. Cartesian-TimeDiff-QRS_beginZ-RY
101. Cartesian-TimeDiff-QRS_beginZ-RZ
102. Cartesian-TimeDiff-QRS_beginZ-QRS_endX
103. Cartesian-TimeDiff-QRS_beginZ-QRS_endY
104. Cartesian-TimeDiff-QRS_beginZ-QRS_endZ
105. Cartesian-TimeDiff-QRS_beginZ-T_beginX
106. Cartesian-TimeDiff-QRS_beginZ-T_beginY
107. Cartesian-TimeDiff-QRS_beginZ-T_beginZ
108. Cartesian-TimeDiff-QRS_beginZ-TX
109. Cartesian-TimeDiff-QRS_beginZ-TY
110. Cartesian-TimeDiff-QRS_beginZ-TZ
111. Cartesian-TimeDiff-QRS_beginZ-T_endX
112. Cartesian-TimeDiff-QRS_beginZ-T_endY
113. Cartesian-TimeDiff-QRS_beginZ-T_endZ
114. Cartesian-TimeDiff-RX-RY
115. Cartesian-TimeDiff-RX-RZ
116. Cartesian-TimeDiff-RX-QRS_endX
117. Cartesian-TimeDiff-RX-QRS_endY
118. Cartesian-TimeDiff-RX-QRS_endZ
119. Cartesian-TimeDiff-RX-T_beginX
120. Cartesian-TimeDiff-RX-T_beginY
121. Cartesian-TimeDiff-RX-T_beginZ
122. Cartesian-TimeDiff-RX-TX
123. Cartesian-TimeDiff-RX-TY
124. Cartesian-TimeDiff-RX-TZ
125. Cartesian-TimeDiff-RX-T_endX
126. Cartesian-TimeDiff-RX-T_endY
127. Cartesian-TimeDiff-RX-T_endZ
128. Cartesian-TimeDiff-RY-RZ
129. Cartesian-TimeDiff-RY-QRS_endX 130. Cartesian-TimeDiff-RY-QRS_endY
131. Cartesian-TimeDiff-RY-QRS_endZ
132. Cartesian-TimeDiff-RY-T_beginX
133. Cartesian-TimeDiff-RY-T_beginY
134. Cartesian-TimeDiff-RY-T_beginZ
135. Cartesian-TimeDiff-RY-TX
136. Cartesian-TimeDiff-RY-TY
137. Cartesian-TimeDiff-RY-TZ
138. Cartesian-TimeDiff-RY-T_endX
139. Cartesian-TimeDiff-RY-T_endY
140. Cartesian-TimeDiff-RY-T_endZ
141. Cartesian-TimeDiff-RZ-QRS_endX
142. Cartesian-TimeDiff-RZ-QRS_endY
143. Cartesian-TimeDiff-RZ-QRS_endZ
144. Cartesian-TimeDiff-RZ-T_beginX
145. Cartesian-TimeDiff-RZ-T_beginY
146. Cartesian-TimeDiff-RZ-T_beginZ
147. Cartesian-TimeDiff-RZ-TX
148. Cartesian-TimeDiff-RZ-TY
149. Cartesian-TimeDiff-RZ-TZ
150. Cartesian-TimeDiff-RZ-T_endX
151. Cartesian-TimeDiff-RZ-T_endY
152. Cartesian-TimeDiff-RZ-T_endZ
153. Cartesian-TimeDiff-QRS_endX-QRS_endY
154. Cartesian-TimeDiff-QRS_endX-QRS_endZ
155. Cartesian-TimeDiff-QRS_endX-T_beginX
156. Cartesian-TimeDiff-QRS_endX-T_beginY
157. Cartesian-TimeDiff-QRS_endX-T_beginZ
158. Cartesian-TimeDiff-QRS_endX-TX
159. Cartesian-TimeDiff-QRS_endX-TY
160. Cartesian-TimeDiff-QRS_endX-TZ
161. Cartesian-TimeDiff-QRS_endX-T_endX
162. Cartesian-TimeDiff-QRS_endX-T_endY
163. Cartesian-TimeDiff-QRS_endX-T_endZ
164. Cartesian-TimeDiff-QRS_endY-QRS_endZ
165. Cartesian-TimeDiff-QRS_endY-T_beginX
166. Cartesian-TimeDiff-QRS_endY-T_beginY
167. Cartesian-TimeDiff-QRS_endY-T_beginZ
168. Cartesian-TimeDiff-QRS_endY-TX
169. Cartesian-TimeDiff-QRS_endY-TY
170. Cartesian-TimeDiff-QRS_endY-TZ
171. Cartesian-TimeDiff-QRS_endY-T_endX
172. Cartesian-TimeDiff-QRS_endY-T_endY

Fig. 11B

173. Cartesian-TimeDiff-QRS_endY-T_endZ
174. Cartesian-TimeDiff-QRS_endZ-T_beginX
175. Cartesian-TimeDiff-QRS_endZ-T_beginY
176. Cartesian-TimeDiff-QRS_endZ-T_beginZ
177. Cartesian-TimeDiff-QRS_endZ-TX
178. Cartesian-TimeDiff-QRS_endZ-TY
179. Cartesian-TimeDiff-QRS_endZ-TZ
180. Cartesian-TimeDiff-QRS_endZ-T_endX
181. Cartesian-TimeDiff-QRS_endZ-T_endY
182. Cartesian-TimeDiff-QRS_endZ-T_endZ
183. Cartesian-TimeDiff-T_beginX-T_beginY
184. Cartesian-TimeDiff-T_beginX-T_beginZ
185. Cartesian-TimeDiff-T_beginX-TX
186. Cartesian-TimeDiff-T_beginX-TY
187. Cartesian-TimeDiff-T_beginX-TZ
188. Cartesian-TimeDiff-T_beginX-T_endX
189. Cartesian-TimeDiff-T_beginX-T_endY
190. Cartesian-TimeDiff-T_beginX-T_endZ
191. Cartesian-TimeDiff-T_beginY-T_beginZ
192. Cartesian-TimeDiff-T_beginY-TX
193. Cartesian-TimeDiff-T_beginY-TY
194. Cartesian-TimeDiff-T_beginY-TZ
195. Cartesian-TimeDiff-T_beginY-T_endX
196. Cartesian-TimeDiff-T_beginY-T_endY
197. Cartesian-TimeDiff-T_beginY-T_endZ
198. Cartesian-TimeDiff-T_beginZ-TX
199. Cartesian-TimeDiff-T_beginZ-TY
200. Cartesian-TimeDiff-T_beginZ-TZ
201. Cartesian-TimeDiff-T_beginZ-T_endX
202. Cartesian-TimeDiff-T_beginZ-T_endY
203. Cartesian-TimeDiff-T_beginZ-T_endZ
204. Cartesian-TimeDiff-TX-TY
205. Cartesian-TimeDiff-TX-TZ
206. Cartesian-TimeDiff-TX-T_endX
207. Cartesian-TimeDiff-TX-T_endY
208. Cartesian-TimeDiff-TX-T_endZ
209. Cartesian-TimeDiff-TY-TZ
210. Cartesian-TimeDiff-TY-T_endX
211. Cartesian-TimeDiff-TY-T_endY
212. Cartesian-TimeDiff-TY-T_endZ
213. Cartesian-TimeDiff-TZ-T_endX
214. Cartesian-TimeDiff-TZ-T_endY
215. Cartesian-TimeDiff-TZ-T_endZ 216. Cartesian-TimeDiff-T_endX-T_endY
217. Cartesian-TimeDiff-T_endX-T_endZ
218. Cartesian-TimeDiff-T_endY-T_endZ
219. areaQuotient_RT_3D
220. QRS-LoopArea
221. T-LoopArea
222. XQRS-1DIntegral
223. YQRS-1DIntegral
224. ZQRS-1DIntegral
225. XT-1DIntegral
226. YT-1DIntegral
227. ZT-1DIntegral
228. QuotientQRS_XY
229. QuotientQRS_XZ
230. QuotientQRS_YZ
231. QuotientT_XY
232. QuotientT_XZ
233. QuotientT_YZ
234. QRS-MagIntegral
235. T-MagIntegral
236. areaQuotient_RT_int
237. InterBeatTimeDiffX-QRS_beginX
238. InterBeatTimeDiffX-RX
239. InterBeatTimeDiffX-QRS_endX
240. InterBeatTimeDiffX-T_beginX
241. InterBeatTimeDiffX-TX
242. InterBeatTimeDiffX-T_endX
243. InterBeatTimeDiffY-QRS_beginY
244. InterBeatTimeDiffY-RY
245. InterBeatTimeDiffY-QRS_endY
246. InterBeatTimeDiffY-T_beginY
247. InterBeatTimeDiffY-TY
248. InterBeatTimeDiffY-T_endY
249. InterBeatTimeDiffZ-QRS_beginZ
250. InterBeatTimeDiffZ-RZ
251. InterBeatTimeDiffZ-QRS_endZ
252. InterBeatTimeDiffZ-T_beginZ
253. InterBeatTimeDiffZ-TX
254. InterBeatTimeDiffZ-T_endZ
255. Mag-Val-QRS_begin
256. Mag-Val-R
257. Mag-Val-QRS_end
258. Mag-Val-T_begin

Fig. 11C

259. Mag-Val-T
260. Mag-Val-T_end
261. Azi-Val-QRS_begin
262. Azi-Val-R
263. Azi-Val-QRS_end
264. Azi-Val-T_begin
265. Azi-Val-T
266. Azi-Val-T_end
267. Ele-Val-QRS_begin
268. Ele-Val-R
269. Ele-Val-QRS_end
270. Ele-Val-T_begin
271. Ele-Val-T
272. Ele-Val-T_end
273. azi_RR_norm
274. azi_no_norm
275. ele_RR_norm
276. ele_no_norm
277. mag_RR_norm
278. mag_no_norm
279. muQRS
280. sigmaQRS
281. muT
282. sigmaQRS
283. superpositionT-QRS
284. sanzangle
285. age
286. weight
287. height
288. BMI
289. NaN_number
290. CrossCor_features(1)
291. CrossCor_features(2)
292. CrossCor_features(3)

Fig. 11D

| | Statisics |
|---|---|
| 1 | Mean Value |
| 2 | Variance |
| 3 | Kurtosis |
| 4 | Skew |
| 5 | 5% Quantile |
| 6 | 95% Quantile |

Fig. 12

METHOD AND DEVICE FOR CARDIAC MONITORING

This nonprovisional application is a continuation of International Application No. PCT/DE2019/100808, which was filed on Sep. 10, 2019 and which claims priority to German Patent Application No. 10 2018 121 974.1, which was filed in Germany on Sep. 10, 2018 and which are both herein incorporated by reference.

BACKGROUND OF THE INVENTION

Field of the Invention

The present invention relates to a method for early detection of the presence of coronary heart disease or cardiac arrhythmia of a patient to be screened, a device, a method for determining and displaying a space vector based on the heart representing the vector of the electrical field formed by the cardiac activity, and a cardiac monitoring method.

DESCRIPTION OF THE BACKGROUND ART

Among the most common diseases in patients is coronary heart disease, CHD for short. The current prevalence of this disease in Germany (about 30% in men and 15% in women) shows that there is a great need for devices with which such problems can be quickly detected and people or patients can be given early treatment or consultations. Another large field of disorders in the activity of the heart is arrhythmia or cardiac arrhythmia. The human heart has a complicated excitation system, which is the driver of cardiac movement. Due to the division of the heart into ventricles and atria, it is necessary to regulate blood flow by muscular contractions. In connection with the rhythmic contraction of the heart muscle, the excitation system includes special muscle cells, which are able to spontaneously de- and repolarize themselves. This way, a rhythm that is primarily generated by the sinus node can be maintained. If this excitation system is disturbed, the heart's pumping capacity is impaired, resulting in supply shortfalls. Not all symptoms are life-threatening, but once they occur frequently they can become good indicators of impending life-threatening conditions.

The reference standard for the detection of CHD is coronary angiography, but this moves away from early screening for CHD. In this procedure, a catheter is inserted into the heart to measure the pressure of the aorta. Contrast media is also used to allow for visualization of the coronary arteries of the heart. Accordingly, it is an invasive method with the associated health risks. Alternatives to this are angiography using CT and MRI. These alternatives also use contrast media, with the associated health risks. These methods are disadvantageous and associated with great effort and high cost.

Measured against the gold standard of coronary diagnostics, coronary angiography, which has a specificity and sensitivity of 100%, noninvasive procedures such as resting ECG and resting echocardiography show a clearly lower sensitivity and specificity (less than 30% and 70%, respectively). Only under stress do these increase for both methods, but each requires the presence of a physician. Furthermore, in the case of stress echocardiography, the results are additionally examiner-dependent. In addition, both of these procedures require a period of at least 15-30 minutes. Other non-invasive procedures such as myocardial perfusion scintigraphy (MPS), coronary computed tomography (CCT) or cardiac magnetic resonance imaging (MRI) require considerable equipment and personnel, the presence of a physician, and they also represent significant cost.

For non-invasive screening of patients, an ECG test can be performed. In this respect, modern software systems offer physicians many tools with which to assess the patient at least quickly. Nevertheless, the evaluation of an ECG significantly depends on the experience of the attending physician and is therefore uncertain. Furthermore, overworking of physicians can lead to misdiagnoses. To solve this problem, automatic measurement systems have been established in the field of ECG analysis. However, these automatic systems are limited to the measurement of ECGs and thus map the experience or defined parameters (e.g. QT interval or ST elevation) in the software. Thus, only the uncertainty in respect of the human factor has been removed.

The parameters of an ECG, especially at rest, are usually insufficient to detect CHD. For this reason, a stress ECG is performed in patients to enable early detection of CHD. For this, it is necessary that the patient is exposed to physical exertion. This provokes the symptoms that can lead to a heart attack. This means that the presence of a physician is always required for such a measurement. The disadvantage of such a procedure lies in the risks involved. Apart from the risk to the patient, it is not possible for all people to undergo such tests. In particular in the risk groups (diabetes, overweight, old age), people are not always able to even achieve the necessary exertion, for lack of sufficient physical fitness. Alternatively, there is exertion by medication and then examination by echocardiography (stress echo) using ultrasound. However, the echo is more suitable in the screening for movement disorders and also does not offer the certainty of an automatic evaluation.

With currently available ECG equipment, it is not possible to detect early signs of CHD or to present them to the physician in a suitable form. All devices known to date have in common that they display several outgoing leads simultaneously, usually with 3 to 12 channels. The display software usually allows for a configuration of the display, which allows for a physician to focus on individual leads and evaluate them according to known guidelines. Suspicion of impending myocardial infarction (the result of untreated CHD) occurs, among others, in ST elevations >=0.1 mV in at least two limb leads and >=0.2 mV in two adjacent chest wall leads. However, the absence of this elevation does not mean that a myocardial infarction has been ruled out, because the vast majority of myocardial infarctions are non-ST elevation myocardial infarctions (NSTEMI).

EP 86 429 B1, which corresponds to U.S. Pat. No. 4,569,357, discloses a method for cardiogoniometry, which pertains to the class of vectorcardiometry methods. This method allows for very accurate determination of the sum vector representing the electric field of the heart and represents it in a Cartesian coordinate system aligned with the heart long axis (instead of the body axis). Here, the potentials that are maximally achieved during depolarization and repolarization (R- and T-loop) of the myocardium are used to diagnose cardiac disease, as well as the directions of the corresponding two vectors labeled in terms of potential and the solid angle between the two labeled vectors. This means that for diagnostic purposes in respect of the values, the labeled vectors and, separately therefrom, their directions and individual components are parameterized in Cartesian coordinates, spherical coordinates and cylindrical coordinates.

The lead points of cardiogoniometry according to EP 86 429 B1, between which potential differences are measured, are:

E1 corresponding to the point for the voltage V4 (according to Wilson),
E2 sagittal to E1 and corresponding to the point for the voltage V8 (according to Wilson),
E3 perpendicular to the path E1-E2, above E1 at a distance of 0.7 times the distance between E1 and E2,
E4 horizontally from E3 toward the right patient side at a distance of 0.7 times the distance between E1 and E2.

A vector addition of the measured potential differences results in a space vector V or in projections of the space vector V on an x, y, and z axis, wherein the x axis is parallel to the line E1-E2, and the y axis is parallel to the line E1-E4, and wherein the z axis is perpendicular to the plane spanned by E1, E2, and E4 (oblique-sagittal plane).

Electrical cardiac action generates an electrical field which varies overtime. The space vector V determined according to EP 86 429 B1 is an approximation to the actual spatial sum vector of this field. Thereby, the direction of the space vector corresponds to the field direction and the length (value or potential) of the space vector corresponds to the field strength. The three voltages X, Y and Z [mV] represent the partial vectors or components of the space vector V in a three-dimensional Cartesian coordinate system, preferably the space vector determined by the cardiogoniometry method in the aforementioned coordinate system. The potential is calculated as a square root of $(X^2+Y^2+Z^2)$.

WO 99/36860 discloses that the course of the value of the space vector V is divided into the ranges R+, R−, ST, T+ and T− by determining the maxima and minima (zeros in the course of the differential quotient). In these ranges, the periodically registered vector values are added up and the integral values determined in this way are further used for diagnostic purposes. This means that the sums of vector values are parameterized in loops.

Furthermore, a method for generating cardiometry parameters is known from WO 03/057031 A1, which can be used in particular for diagnostic purposes when screening the human heart. Such a method is known in WO 03/057031 A1 as "vectorcardiometry" and serves for the generation of cardiometry parameters from a vector which represents the electric field of the heart and which is determined, e.g., according to known vectorcardiometry methods. The space vector is represented starting from a coordinate origin, wherein a spatial trajectory described by the vector apex and/or a spatial velocity of the vector apex moving along the trajectory is parameterized in the virtual space around the coordinate origin. The parameters generated in this way, or the deviations mentioned, are particularly suitable for the diagnosis of cardiac disease or disorders.

The above-mentioned methods for determining and displaying a space vector related to the heart according to cardiogoniometry, in particular according to EP 86 429 B1, are subject to the disadvantage that electrodes or sensors must be attached to the human body at points that exactly correspond to the four lead points E1-E4 at which potential differences are measured. An incorrect position of an electrode, in particular at the lead point E1, leads to a distortion of the measured values, so that the analysis obtained is unusable and a reliable diagnosis for a screened heart is not possible.

Another disadvantage with the technologies in the prior-art printed publications mentioned above is that automatic analysis with respect to the three-dimensional signals obtained from a patient is not possible.

SUMMARY OF THE INVENTION

It is therefore an object of the invention to provide a technology in the field of non-invasive cardiac monitoring which allows for improved screening of patients in a shorter period of time, and which in particular also allows for automatic analyses.

In an exemplary embodiment, a method according to the present invention is used for the early detection of the presence of coronary heart disease (CHD) and/or a heart rhythm disorder (HRD) and/or heart valve insufficiency in a patient to be screened, and includes the steps of: non-invasive recording of ECG signals at the patient's heart in the resting state; filter processing of the recorded ECG signals; converting the filtered ECG signals into orthogonalized measured values based on vectorcardiography; and inputting of the orthogonalized measured values into a system based on artificial intelligence (AI), in which they are weighted in a manner determined by known findings data from reference patients via the training of a neural network. The orthogonalized findings data is mapped to a value between −1 and 1 and allows for a patient diagnosis.

Similarly, the invention also provides a device for early detection of the presence of CHD and/or a HRD and/or heart valve insufficiency in a patient being screened, comprising a plurality of sensors positionable on the body of the patient being screened at predetermined lead points to thereby non-invasively detect the presence of ECG signals at the patient's heart, preferably in the patient's resting state, at least one filter with which the recorded ECG signals can be filtered, an evaluation device with which the filtered ECG signals can be converted to orthogonalized measured values on the basis of vectorcardiography, and a system based on artificial intelligence (AI), which has been trained with findings data from reference patients, wherein the orthogonalized measured values are entered into the AI system, and functionally mapped to values between −1 and 1 according to the weighting of the neural network in order to create a diagnosis for the screened patient.

As already explained above, it is again separately pointed out at this point that the above method and the device according to the present invention are also suitable for early detection of the presence of heart valve insufficiency in a patient. In this respect, it is understood that the findings data of the reference patients within the AI system are adapted to this.

The theoretical basis for the principle of analysis according to the present invention is the so-called "vectorcardiography", which makes a significant contribution as a non-invasive method in the field of cardiac ischemia diagnostics.

The invention according to the above method and the above device is based on the essential realization that the representation of the electrophysiological properties of the heart, as compared to the complicated representation of the often used conventional ECG with its up to 12 leads, is simplified by first using vectorcardiography to convert the filtered ECG signals to orthogonalized measured values. Here, the cardiac potentials are measured in an orthogonal system and vectorially added up. With such, a three-dimensional measurement and localization of the cardiac potential, a large number of new parameters can be created or taken into account, which allows, among other things, for the detection of myocardial ischemia.

A significant advantage of the invention is that it performs or makes possible for an automated analysis using three-dimensional signals to be performed. This not only ensures an in-depth basis for analysis, but also enables the electrophysiological properties of the heart to be displayed graphically. Compared to the ECG measurements used up to now and the up to 12 leads (=12 dimensions) used for this purpose, the otherwise complicated representation is greatly simplified and visualized in an intuitive manner, with the present invention resulting in fewer analysis and evaluation errors.

The measurement or non-invasive recording of ECG signals at the patient's heart expediently takes place in the patient's resting condition (i.e. without physical exertion) using four surface electrodes. This means that the ECG signals are recorded at a total of four lead points on the patient's body near the heart. For this measurement, the following display forms can be provided: analog orthogonal projections X, Y, Z to control the technical quality of the measurement; potential, measured in different time intervals of the cardiac cycle; loops in 2D and 3D, for locating the potential in the heart; and/or maximal vectors of atrial and ventricular depolarization and ventricular repolarization.

A central aspect of the present invention is that the orthogonalized measured values are input into a system based on artificial intelligence (AI), preferably in the form of a neural network or a plurality of such neural networks, wherein said AI system (or neural network) has been trained with already known findings and in this respect, these findings data of reference patients are stored in the AI system. By means of a functional mapping of the entered orthogonalized measured values via a neural network to values between −1 and 1, a diagnosis for the screened patient is created, wherein this AI system has been trained with the aid of findings data of reference patients, which weights typical characteristics of the measured values with respect to their relevance for the state of health.

With regard to the known findings data of reference patients, on which the AI system or neural network is based, it is separately emphasized that for these reference patients, there is clear knowledge with regard to their state of health ("healthy" or "sick"). This information may have been obtained by coronary angiography, which provides an unambiguous diagnosis for the reference patients ("healthy" or "sick"), or from other sources. Based on this, a classification and a clustering of the findings data is made (diagnosis as "healthy" or "sick").

The leads between the respective four lead points at which the ECG signals are recorded can be considered both in Cartesian coordinates and in spherical and cylindrical coordinates. Such a conversion into spherical coordinates allows for the determination of the actual time points of the physiological extreme points (i.e. the exact point of the R-peak or T wave) during a heartbeat.

The AI system or the neural network can be trained prior to step (iv). This means that the AI system or the neural network is trained or optimized by inputting specific learning values, wherein the number of these specific learning values can be between 10 and 30, e.g. 20, or in any case significantly fewer than 100. In this context, it should be emphasized that such training by the specific learning values mentioned is not carried out during the actual diagnosis, but in advance, so that the learning values available in the training set can be applied.

In connection with the execution of the method and/or the use of the device according to the present invention, it is pointed out that practically every screened person or user for whom the clear knowledge/information regarding the state of health ("healthy" or "sick", e.g. with the help of coronary angiography) is available, feeds the AI system or the neural network with "fresh" health parameters. New measurement data helps to further optimize the weightings of the neural network so that, with increasing data, an increasingly better classification of sick vs. healthy can take place. The characteristic weightings between the neurons in the AI system are adjusted from the training set with each new patient so that errors of past diagnoses are minimized.

In this way, the AI system or the neural network learns more with each piece of information and thus optimizes itself permanently, if a training of the AI system is carried out before the actual diagnosis of a patient, namely on the basis of the data of persons whose state of health is clearly known. As a result, the diagnosis of a single sensor is compared with the diagnoses of countless sensor information/users (also historically). The accuracy and thus the meaningfulness of the measurement results are thus—in training mode—permanently optimized and improve with each individual measurement, namely in relation to a person whose state of health is known. In this respect, it is separately pointed out that the AI system or a neural network is not a single system or network, but a continuously increasing number of such systems or networks. Accordingly, the invention provides for the integration of a plurality of such AI systems or neural networks, for example in the form of a comprehensive large-scale neural network based on a constantly growing number of neural networks.

The aforementioned aspect of the training using specific learning values also applies for the device according to the invention. This means that its AI system or neural network is trained in the manner described above by inputting specific learning values before a patient is screened in practice and a subsequent diagnosis is made on the basis of the measured values.

The training of the AI system or a neural network by inputting said specific learning values is based on the fact that in this case, ECG signals are recorded or processed in patients for whom a clear knowledge/information regarding the state of health ("healthy" or "sick", e.g. with the aid of coronary angiography)) is available. Further details regarding the implementation of such training will be explained separately below in connection with an associated embodiment of the invention.

The present invention also provides a method for determining and displaying a space vector related to the heart, which represents the vector of the electrical field formed by the activity of the heart.

Here, measured values of the heart are recorded on the body at a first lead point, at a second lead point, at a third lead point and at a fourth lead point, wherein potential differences are measured in the form of an anterior lead between the first lead point and the fourth lead point, a dorsal lead between the second lead point and the fourth lead point, a horizontal lead between the third lead point and the fourth lead point, a vertical lead between the first lead point and the third lead point, and an inferior lead between the first lead point and the second lead point. An orthogonal system is formed with the relationships:

$$x = D \cos 45° - I$$

$$y = D \sin 450 + A$$

$$z = (V-H)\sin 450$$

and the measured values and the space vector determined therefrom are mapped in this orthogonal system (x, y, z). Subsequently, the following steps are run through in this method:

(a) Performing a measurement on a patient using the first to fourth lead points on the patient's body to obtain a cardiogram for this patient, (b) Extracting the amplitudes of the R wave from the cardiogram of step (a) for each heartbeat in the x, y and z direction, (c) Determining mean values $\mu x$, $\mu y$, $\mu z$ and standard deviations $\sigma x$, $\sigma y$, $\sigma z$ of the respective amplitudes recorded in millivolts from the cardiogram in step (b), wherein a calculation vector using these mean values $\mu x$, $\mu y$, $\mu z$ and standard deviations $\sigma x$, $\sigma y$, $\sigma z$ is then formed, (d) Forming a coefficient matrix obtained on the basis of a Principal Component Analysis for measurements in reference patients using different formats, (e) Multiplying the calculation vector in step (c) by the coefficient matrix in step (d) to obtain a resulting vector with a total of six main axes, (f) Extracting the first main axis and the second main axis from the resulting vector in step (e), to form a reference point in the space of the first and second main axis, (g) Determining a Euclidean distance of the reference point from a predetermined target point, which corresponds to a correct position of the four lead points on the human body, (h) if the distance of the reference point from the predetermined target point is greater than a predetermined maximum value: performing an angular correction for a first triangle formed by the first lead point, the third lead point and the fourth lead point, and for a second triangle formed by the first lead point, the second lead point and the fourth lead point, so that the Euclidean distance between the reference point and the predetermined target point is minimized by adapting the orthogonal system (x, y, z) to the changed geometry.

The latter method according to the invention is based on the essential knowledge that, on the basis of, on the one hand, the knowledge of a correct position for the four lead points and, on the other hand, of a Principal Components Analysis, it is possible to compensate for an incorrect position of an electrode assigned, in particular, to the first lead point, such that the patient's measurements obtained can still be used and enable a realistic diagnosis for the patient being screened to be made.

In an advantageous further development of the invention, the last-mentioned method can provide that the predetermined target point is selected from a target area determined on the basis of mean values and standard deviations of a plurality of measurements prior to performing step (h). This means that these measurements are used to obtain comparative values for the positions of the electrodes on the human body in order to perform the angular correction according to step (h).

To monitor the heart, in particular in a human being, the present invention also provides a method in which ECG signals are recorded at the heart and, on the basis thereof, a space vector is determined using vectorcardiography, wherein this space vector represents the course of the sum vector of the electrical field of the heart, and has a direction corresponding to the field direction and a length corresponding to the potential. A quotient is formed from the areas which are covered by a length of the space vector (=radius vector) as a function of time during the R wave and during the T wave, respectively, wherein this dimensionless and scalar quotient is subsequently subjected to further evaluation. In the course of this further evaluation, the quotient formed from the area (R wave)/area (T wave) is in each case set with respect to predetermined limit values that are relevant for the clinical picture to be screened. This means that said quotient formed from the area (R wave)/area (T wave) is correlated or compared with at least one predetermined limit value, on the basis of which a diagnosis for the screened patient with regard to a certain clinical picture (e.g. CHD and/or HRS and/or heart valve insufficiency of a patient) is made or can be made.

In an advantageous further development of the latter method, coronary heart disease (CHD) is detected or determined for the screened heart if the quotient formed by the areas covered by the space vector during the R wave and during the T wave, respectively, is $$\text{Area}(R\text{-wave})/\text{Area}(T\text{-wave})=a$$

is not located in the interval $[a_{0,KHK}, a_{1,KHK}]$ or outside this interval: This interval is defined by a lower limit value $a_{0,CHD}$ and by an upper limit value $a_{1,CHD}$. These limits $a_{0,CHD}$ and $a_{1,CHD}$ can be determined as a function of a training set. Furthermore, it is pointed out that the indication "CHD" of the lower and upper limit values $a_{0,CHD}$ and $a_{1,CHD}$ for the present invention is to be understood in the sense that with the aid of these limit values, the clinical picture of coronary heart disease ("CHD"), which is also known as ischemic heart disease ("IHD"), can be recognized.

In the method just discussed according to the present invention, a cardiac arrhythmia (HRD) can also be detected for the screened heart if the quotient formed by the areas covered by the space vector (10) during the R wave and during the T wave, respectively, satisfies the condition of $$\text{Area}(R\text{-wave})/\text{Area}(T\text{-wave})=a_{0,HRD}$$

or $$\text{Area}(R\text{-wave})/\text{Area}(T\text{-wave})=a_{1,HRD}$$

Accordingly, per the last discussed method of the present invention, it is possible, by a comparison of the quotient formed by the areas covered by a length of the space vector (=radius vector) as a function of time during the R wave and during the T wave, respectively, to make an accurate initial diagnosis of a patient's heart being screened, using predetermined values for the parameter "a", with regard to the possible presence of HRD.

Depending on whether the presence of HRD or CHD is to be specifically detected, it is understood that the limit values $a_0$ and $a_1$ are suitable to detect these clinical pictures and thus to compare or correlate the quotient formed from the area (R wave)/area (T-wave), which is based on certain data. In conjunction with an HRD, this can be expressed by the indexing "HRD" (i.e., by $a_{0,HRD}$, $a_{1,HRD}$); in conjunction with a CHD, this can be expressed by the indexing "CHD" (i.e. by $a_{0,CHD}$, $a_{1,CHD}$).

If reliable data for the lower and upper limit values $a_0$, $a_1$ is available for a clinical picture being studied (e.g., HRD and/or CHD), these limit values can be set to these predetermined values prior to screening a patient, in each case depending on whether the presence of HRD or CHD is to be screened. Alternatively, it is possible to use these limit values with the aid of a training set of data sets from a large number of test persons, as will be explained in detail below.

In an advantageous further development of the invention, the lower and upper limit values $a_0$ and $a_1$ can each be determined with the aid of a training set of test person data. Here, the following steps are carried out: (i) Calculating the quotient area (R wave)/area (T wave) for all test persons to obtain ratio time series, (ii) Calculating a mean value (µ) and an associated standard deviation (σ) from the ratio time series of step (i), (iii) Determining the lower limit $a_0$ while considering the mean value (µ) and the standard deviation (σ) of step (ii), by the relationship: $a_0$=mean value (µ)− standard deviation (σ), and/or determining the upper limit $a_1$ while considering the mean value (µ) and the standard deviation (σ) of step (ii), by the relationship:

$a_1$=mean value(µ)+standard deviation(σ).

With respect to the above steps (i) to (iii), it is understood that these are to be associated with a training with which the lower and upper limits $a_0$ and $a_1$ can be determined with great "resilience" in order to subsequently, and on the basis of this, make an actual patient diagnosis for the clinical picture being screened with great accuracy.

For clarification of the above calculation rule in step (iii), let it be pointed out again that the lower limit value $a_0$ is formed by subtracting the mean value µ and the corresponding standard deviation a from each other. On the other hand, the upper limit value $a_1$ is formed by adding the mean value µ and the corresponding standard deviation σ to each other.

With regard to the above-mentioned determination of the lower and upper limits $a_0$ and $a_1$, it is understood that the underlying data of the test persons with which the ratio time series are formed according to step (i) refer to the clinical picture to be screened, HRD and/or CHD, or are relevant for this purpose. For example, to screen for the presence of coronary heart disease ("CHD"), the limit values $a_{0,CHD}$ and $a_{1,CHD}$ are determined only on the basis of data sets from test persons who can be excluded with certainty from having CHD or IHD. Mutatis mutandis, this also applies to the limit values $a_{0,HRD}$, $a_{1,HRD}$ when examining a patient with regard to the presence of HRD.

According to an advantageous further development of the invention, it is provided that for the determination of the lower and upper limit value only the data sets of healthy patients ("- -") are used. As compared to the data sets of sick patients, this has the advantage that the standard deviations of the mean values of the healthy patients are generally smaller, which means that it is possible to recognize the clinical pictures or findings of HRD and/or CHD with greater accuracy or reliability.

In advantageous further embodiment of the invention, particularly with respect to all of the above methods, it can be provided that a t-shirt is used to record the ECG signals, which has four sensors or electrodes that correspond to a correct position of the four lead points on the patient's body. These electrodes may be suitably incorporated into the fabric of the t-shirt. In the same way as a t-shirt can be used for the sensors or electrodes that are to be brought into contact with the patient's body, a portable or mobile sensor system can also be provided, e.g. in the form of a chest strap or the like. It is important that in such a portable sensor system the individual sensors or electrodes are connected to each other to form an assembly and that they are positioned at the respective lead points on the patient's body. This eliminates the need for manually applying the individual sensors to the patient's body.

The aforementioned method(s) of the present invention represent a non-invasive, reproducible, fast and cost-effective diagnostic approach for the detection of hemodynamically relevant stenoses of the coronary arteries at rest. The diagnosis is carried out by a computer-based infinitesimal, three-dimensional computation of the excitation processes of the mammalian heart, based on a specific algorithm in conjunction with an AI system or neural network correlated to the intrinsic blood as well as the specific spatial orientation of the myocardium in the dipole field as a function of time starting from a defined point. With a method according to the invention, it is possible to obtain, in relation to the screened patients, a sensitivity of 95 to over 99% and a specificity of 80 to over 90%. This approach is also referred to by the applicant as "cardisiography".

With respect to the present invention, it is separately emphasized that its implementation is preferably carried out using a computer or comparable computer units. This means, for example, that the system based on artificial intelligence (AI), which is employed in a method and a corresponding device for the early detection of the presence of CHD and/or HRD, is used with the help of a computer or the like. Mutatis mutandis, this also applies to a method in respect of the evaluation of the quotient formed from the area (R wave)/area (T wave), preferably taking into account at least one predetermined limit value.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 12 shows exemplary statistical methods applicable to a method according to FIG. 9.

DETAILED DESCRIPTION

In the following, with reference to FIGS. 1-18, preferred embodiments of the heart monitoring method according to the invention and of a device 10 used for this purpose are shown and explained in detail.

Figure 1:
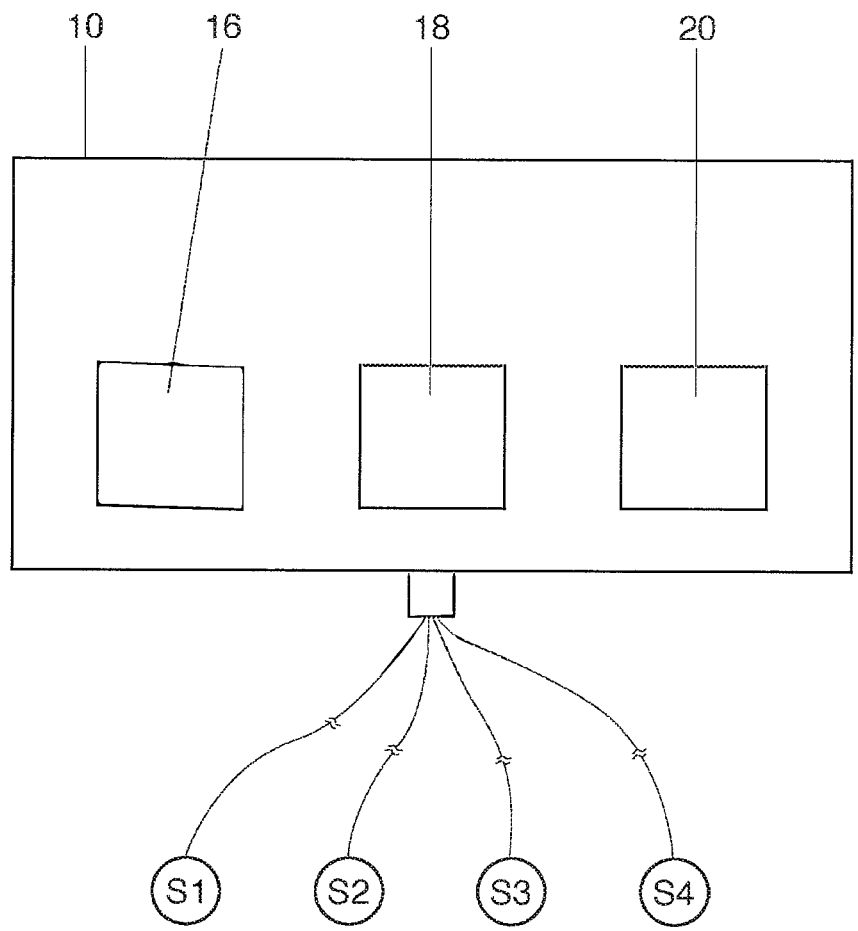
FIG. 1 is a simplified schematic sketch of a device according to the invention for the early detection of CHD or HRD.

The device 10, shown in basically simplified form in FIG. 1, is used in the screening of a patient 11 (cf. FIG. 2) for early detection of the presence of coronary heart disease (CHD) or cardiac arrhythmia (HRD). For this purpose, the device 10 comprises four sensors or electrodes S1, S2, S3, S4, a data filter 16, an evaluation device 18 and a system 20 on the basis of artificial intelligence (AI). The evaluation device 18 is equipped with a memory element (not shown) so that measured signals or values can be stored therein, at least for a short time. The AI system 20 may have at least one neural network 20N (cf. also FIG. 18) or a plurality of such neural networks or be formed from such neural networks.

The sensors S1-S4 are connected for signaling (e.g. via a cable connection, or via a wireless radio link) to the device 10 in such a way that its measured values first pass through the filter 16 and then reach the evaluation device 18. The evaluation device 18 is data-technically connected to the AI system 20 in such a way that the measured values, which are suitably processed by means of the evaluation device 18 or converted into orthogonalized data based on the vectorcardiography, as further specified below, can be entered into the AI system 20. This is done for the purpose of making a diagnosis for the patient 11 being screened using the device 10.

Figure 2A:
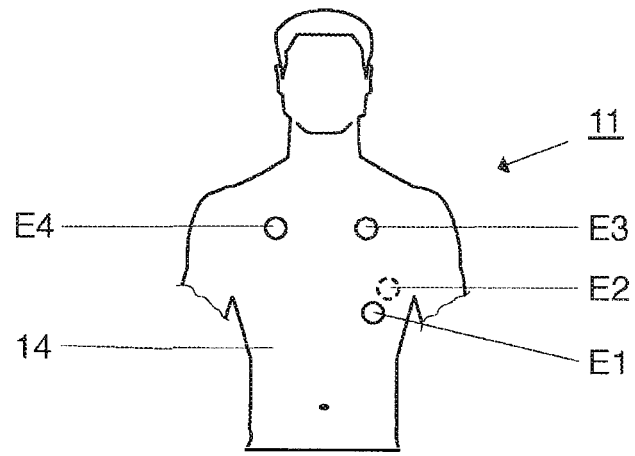
FIG. 2 is a view of a patient from the front (FIG. 2a) and from the back (FIG. 2b)
Figure 2B:
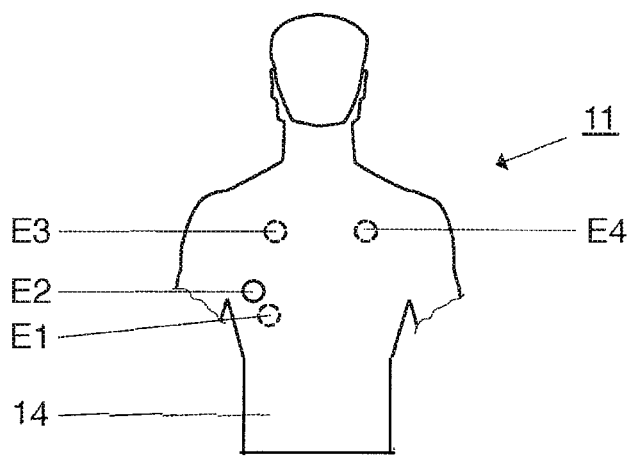

FIG. 2 shows—for an improved understanding of the invention—a patient 11, namely in a front view (FIG. 2a) and in a rear view (FIG. 2b). On the body 14 of the patient 11, a total of four lead points are provided, namely a first lead point E1, a second lead point E2, a third lead point E3 and a fourth lead point E4. The lead points E1, E3 and E4 are each located in the chest region of the patient 11, wherein the lead point E2 is located on the patient's 11 back. In relation to these four lead points E1 to E4, it should be noted that the first sensor S1 is placed at the first lead point E1, the second sensor S2 is placed at the second lead point E2, the third sensor S3 is placed at the third lead point E3, and the fourth sensor S4 is placed at the fourth lead point E4 on the body 14 of the patient 11. Potential differences are measured between these lead points, as explained separately below. For further details on the positions of these individual lead points E1-E4 on the patient's body 14, reference is made to the disclosure according to EP 86 429 B1, the contents of which are hereby referred to in their entirety.

Figure 3A:
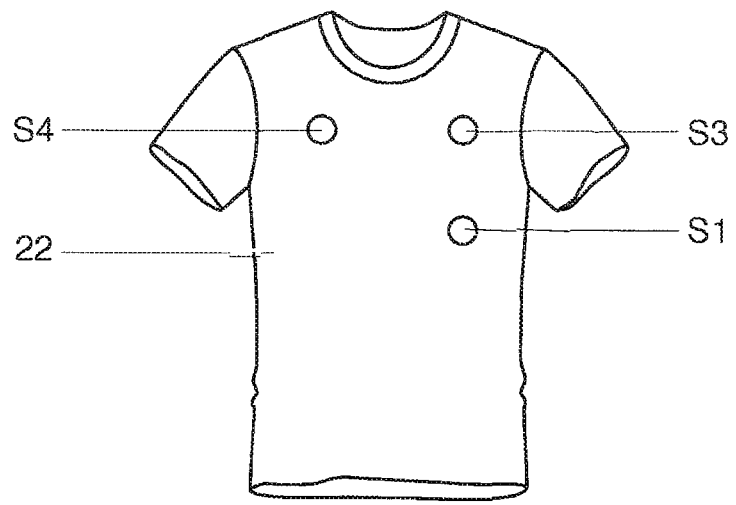
FIG. 3 is a view of a t-shirt from the front (FIG. 3a) and from the back (FIG. 3b), which t-shirt can be used by the device according to FIG. 1, FIG. 4, FIG. 7b show, in each case a front view of a patient, to illustrate an orthogonal system (x, y, z) in which a space vector is mapped according to the present invention.
Figure 3B:
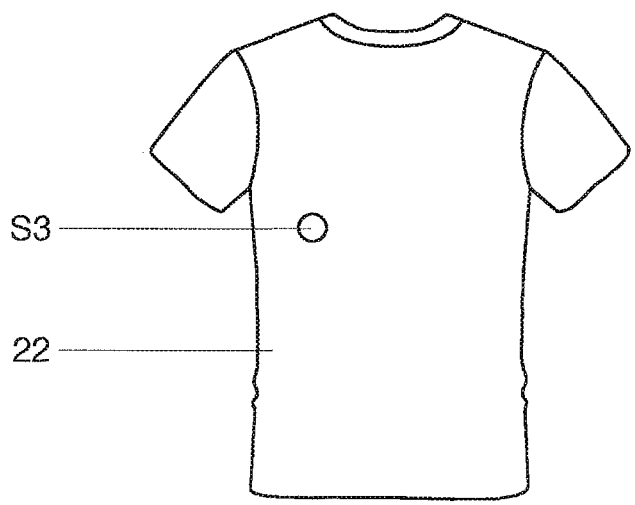

FIG. 3 shows a t-shirt 22 in simplified form. The aforementioned sensors S1-S4 of the device 10 may be integrated into the t-shirt 22, for example by being woven into its textile structure. Such a t-shirt 22 has the advantage that a patient 11 merely puts on or slips over this t-shirt 22 in preparation for an examination, in which case the sensors S1-S4, which are integrated in the t-shirt 22, automatically reach their intended position adjacent to the four lead points E1-E4. The use of such a t-shirt 22 eliminates the need for time-consuming and possibly error-prone manual application of the individual sensors S1-S4 to the body 14 of the patient 11. As an alternative to the t-shirt 22, it is also possible to use a (not shown) chest strap to which the sensors or electrodes S1-S4 are attached.

To screen a patient 11 or to obtain a set of test data for training the AI system 20, the four sensors S1-S4 are positioned on the human body 14 at the assigned four lead points E1-E4. Subsequently, in the resting state of the patient 11, ECG signals are recorded at the heart 12 of the patient 11 with the aid of the sensors S1-S4 brought into position. The ECG signals are then passed through the filter 16 and subsequently converted in the evaluation unit 18 into orthogonalized measured values (in the axes x, y, z) according to the Sanz system per EP 86 429 B1.

Figure 4:
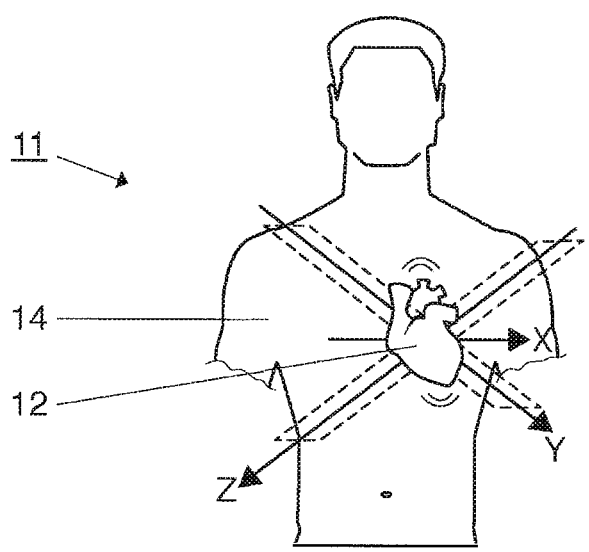
Figure 5A:
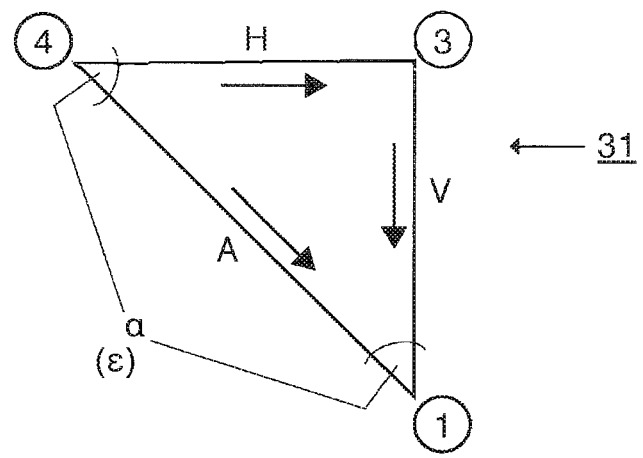
FIG. 5 is schematic simplified views of a first triangle (FIG. 5a) and a second triangle (FIG. 5b), based on which, in respect of the orthogonal system according to FIG. 4, an angular correction is carried out according to the invention.
Figure 5B:
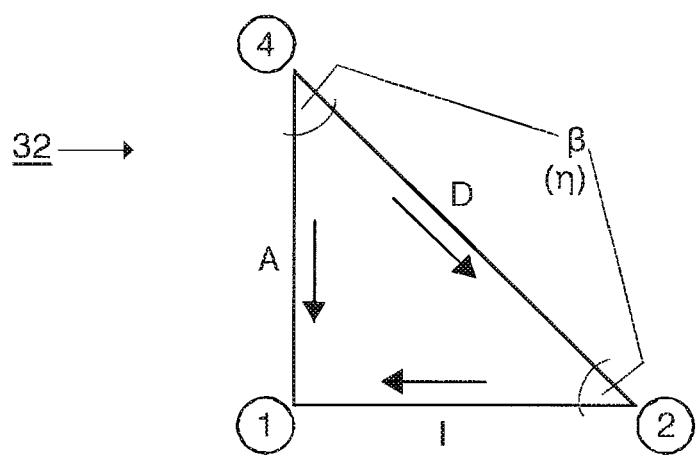

FIG. 4 illustrates the axes x, y, z according to the Sanz system, in relation to the body 14 of a patient 11 and his heart 12. In this respect, reference is also made to FIG. 5, wherein in FIG. 5a a first triangle 31 is schematically illustrated, which is located between the lead points E1; E3 and E4, and FIG. 5b illustrates a second triangle 32, which is selected between the lead points E1, E2 and E4. The meaning of these two triangles 31, 32 will be explained separately below.

As already explained, potential differences are recorded between the individual lead points E1-E4. In detail, these are an anterior lead A between the first lead point E1 and the fourth lead point E4, a dorsal lead D between the second lead point E2 and the fourth lead point E4, a horizontal lead H between the third lead point E3 and the fourth lead point E4, a vertical lead V between the first lead point E1 and the third lead point E3, and finally an inferior lead I between the first lead point E1 and the second lead point E2. The first lead point E1, the third lead point E3 and the fourth lead point E4—as shown in FIG. 5a—form a first triangle 31, wherein a second triangle 32—as shown in FIG. 5b—is formed from the first lead point E1, the second lead point E2 and the fourth lead point E4. The mentioned leads with their designations A, D, H, V and I are also shown in FIG. 5a and FIG. 5b. For further correlations on these leads, reference is made to the content of EP 86 429 B1.

The meaning of the first and second triangles 31, 32 is explained separately elsewhere below in connection with a so-called "correction method" according to the present invention.

When an ECG measurement is performed, the electrical measured values of the leads A, D, H, V and I mentioned above enter the device 10 and are further processed therein accordingly, as already explained above.

Figure 6:
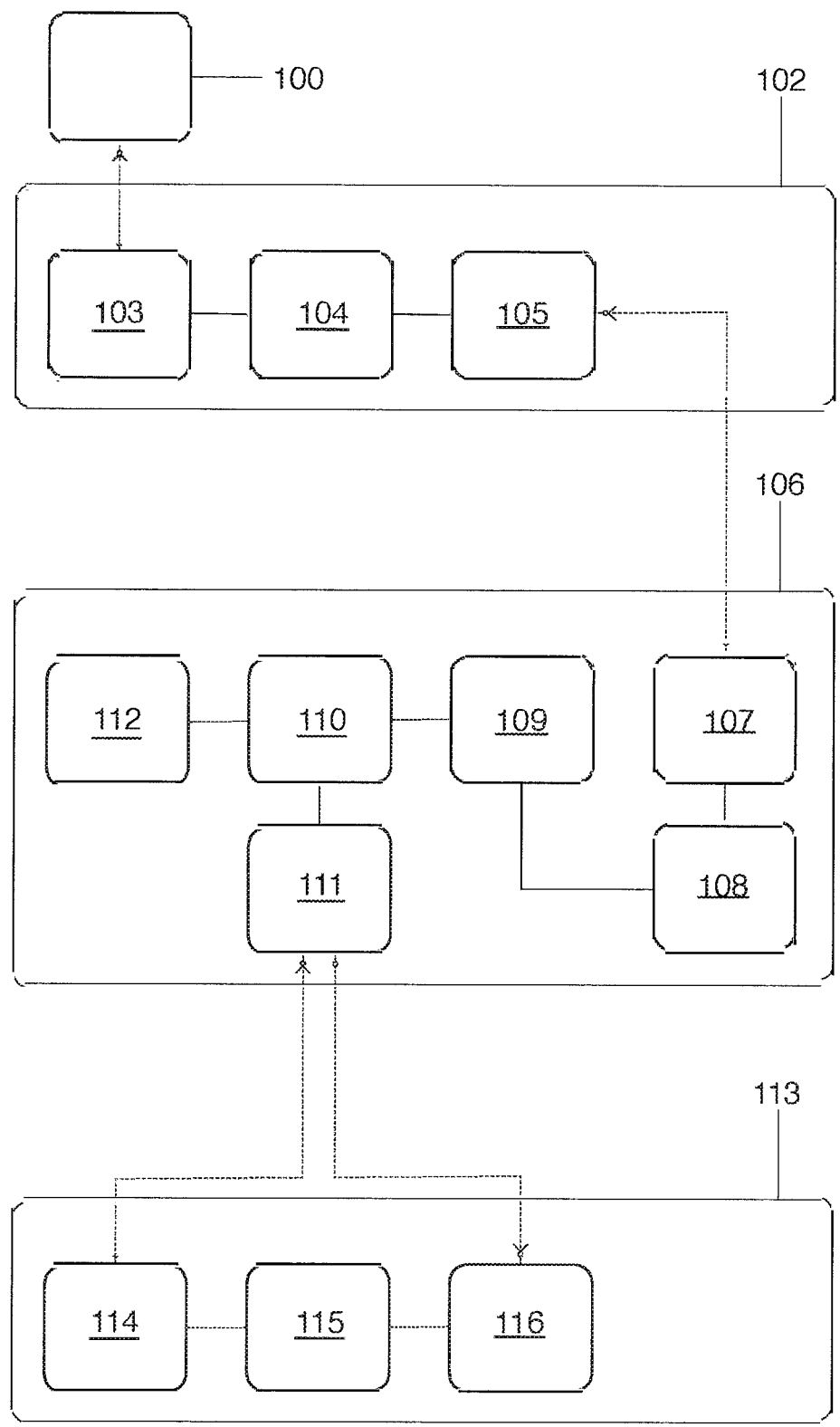
FIG. 6 is a generally simplified view of a system architecture according to the invention, within which the device of FIG. 1 according to the invention is used.

With reference to FIG. 6, further details of the device 10 and its integration into an overall architecture in accordance with the invention for carrying out the present invention are explained below. In detail:

The architecture according to FIG. 6 provides the following components: sensing device 100, data recorder 102, Cardisio® device 106, and server 113. The data recorder 102 includes a signal receiver 103, a signal converter 104, and a signal memory 105. The Cardisio device 106 includes a signal reader 107, a vector data generator 108, a vector data memory 109, a vector data evaluator 110, a vector data synchronizer 111 and a vector data display 112. The server includes 113 a vector data memory 114, a vector data analyzer 115, and a vector data evaluation memory 116.

The sensing device 100 is made up by the four sensors or electrodes S1-S4 of the device 10 mentioned above.

The sensing device 100 and the data recorder 102 are the components or parts of the device 10 that are used to measure or record the ECG signals. Hereby, the analog ECG signals are received, processed and suitably converted into digital signals. As already explained, the digital signals can be stored at least briefly in the memory element of the evaluation device 18—in this case in the form of the signal memory 105.

The Cardisio device 106 reads the digital signals from the data recorder 102 using the vector data generator 108 to determine vector data based on the digital signals. The vector data generated in this way is then stored in the vector data memory 109. Based on this, the vector data evaluator 110 generates a representation of this vector data, e.g. in the form of a three-dimensional curve, wherein this representation is then shown or visualized by means of the vector data display 112.

The architecture of FIG. 6 further illustrates that within the Cardisio device 106, the vector data evaluator 110 is signal-connected to the vector data synchronizer 111, and the latter is connected to the server 113 via a signal path or link. Hereby, the vector data generated can first be read into the vector data memory 114 on the server 113 via the vector data synchronizer 111. Subsequently, by means of the vector data analyzer 115, it is possible to carry out a targeted evaluation of large data volumes or the generated vector data, and to perform statistical analyses in this respect. Finally, the manual and/or automatic evaluations of the data sets are stored in the vector data evaluation memory 116, from which these evaluations can be uploaded back to the device 106, e.g. for display on or with the vector data display 112.

It is understood that the components and parts of the sensing device 100, the data recorder 102, the Cardisio device 106 and the server 113 explained in FIG. 6 are each parts of the device 10 according to the invention. In particular, the vector data evaluation memory 116 is part of the AI system 20 or of a neural network $20_N$, wherein already known findings data of reference patients is stored herein, in respect of which a clear diagnosis ("healthy" or "sick") is known.

Figure 7A:
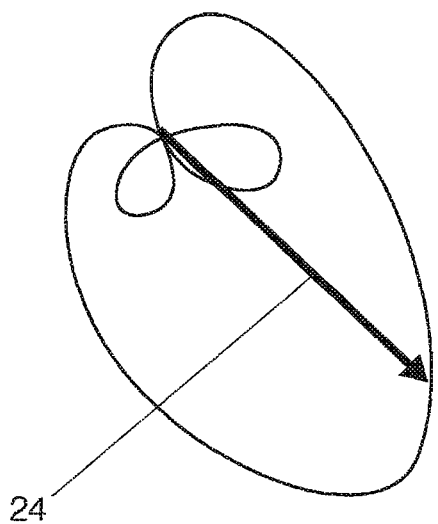
FIG. 7a is a generally simplified representation of a space vector formed during activity of the human heart.
Figure 7B:
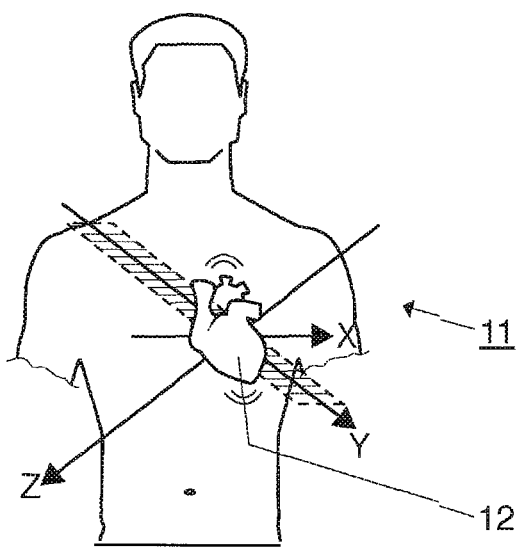

Based on the ECG measured data recorded using the four sensors S1-S4 at the heart 12 of a patient 11, a space vector 24, which shows the electrical activity of the heart 12, can be generated by the evaluation device 18. Specifically, this space vector 24 forms the course of the sum sector of the electrical field of the heart 12 and has a direction corresponding to the field direction and a length corresponding to the potential. An example of such a space vector 24 is shown in FIG. 7a, which is preferably mapped in an orthogonal system, which is formed from the axes x, y, z according to the Sanz system (per EP 86 429 B1). FIG. 7b again shows—in the same way as FIG. 4—in a simplified manner the heart 12 of a patient 11, in connection with the axes x, y, z according to the Sanz system.

A method according to the present invention is explained below with reference to FIG. 8, which shows a flow chart of the steps of such a method. In detail:

At the beginning of the method, the sensors S1-S4 of the device 10 described above (cf. FIG. 1) are placed on the upper body of a patient 11, namely in accordance with the four lead points E1, E2, E3 and E4 (cf. FIG. 2a, FIG. 2b). The t-shirt 22 of FIG. 3 can be used for this purpose. In this way, ECG signals are recorded in a non-invasive manner at the patient's 11 heart 12, namely in the resting state of the patient 11. This corresponds to step (i) of the method according to FIG. 8.

Subsequently, in step (ii) of the method shown in FIG. 8, the recorded ECG signals are filtered, namely, as explained with reference to FIG. 1, by the filter 16. Such filtering serves to eliminate high-frequency noise and low-frequency interference (e.g. caused by the patient's breathing). Examples of filter types are notch filters, high pass filters, Savitzky-Golay low-pass filters.

Figure 8:
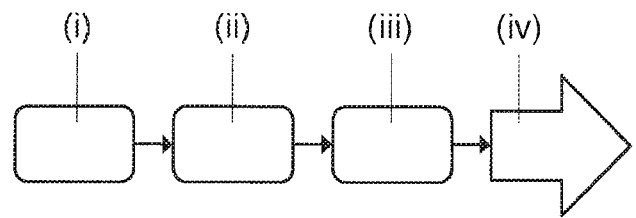
FIG. 8 is a flow chart in which a method according to the present invention is carried out.

In the subsequent step (iii) of the method shown in FIG. 8, the filtered ECG signals are then converted into orthogonalized measured values on the basis of vectorcardiography by means of the evaluation device 18, which is signal-connected to the filter 16. Significant areas in the signal of a heartbeat are localized, e.g. beginning and end of the QRS complex, beginning, maximum and end of the T wave. To determine the actual times of the physiological extreme points, it is advantageous when said leads A, D, H, I and V obtained between the lead points E1-E4 (cf. FIG. 2a, FIG. 2b) are each converted into spherical coordinates.

Finally, in a further step (iv) of the method according to FIG. 8, the orthogonalized measured values are entered into the AI system 20 or a neural network $20_N$. It should be noted that the AI system 20 is based on already known findings data of reference patients for whom—as already explained above—there is clear knowledge with regard to their state of health ("healthy" or "sick"). On the basis of this, it is then possible, by means of the vector data analyzer 115 and the vector data evaluation memory 116, to provide a diagnosis for the screened patient 11 by comparing the entered orthogonalized measured values with the findings data of the reference patients within the AI system 20.

For step (i) of the method of FIG. 8, it is recommended that a non-invasive recording of ECG signals be performed at the heart 12 of the patient 11 at exactly the four lead points E1-E4 described above with reference to FIG. 2a and FIG. 2b.

Figure 9:
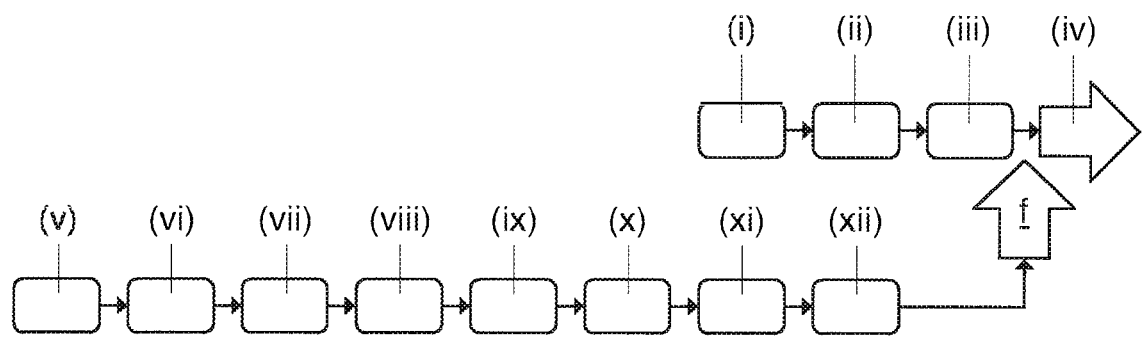
FIG. 9 is a flow chart in which a method according to the present invention is carried out according to a further embodiment.

By means of an advantageous further development or supplementation of the method of FIG. 8, it is possible to train the AI system 20 or the neural network $20_N$ prior to step (iv), namely by inputting specific learning values f. This is shown in FIG. 9 and explained in detail below:

The number of specific learning values f with which the AI system 20 or the neural network $20_N$ is trained prior to step (iv) can be between 10 and 30, and e.g. assume the value of 20. These specific learning values f are determined by the following step sequence:

(v) Providing measured values of a set M (cf. FIG. 10) of patients 11 with a known finding, wherein these measured values are orthogonalized on the basis of vectorcardiography, (vi) Providing a plurality of time series parameters (cf. FIG. 11a and FIG. 11b) and at least one statistical method (cf. FIG. 12), (vii) Forming a 3D matrix 25 (cf. FIG. 10a), wherein the orthogonalized measured values of the set (M) of patients define the rows, the time series parameters define the columns and the time series length defines the depth of this matrix (25), wherein in the case of scalar parameters, the depth is equal to one, (viii) Classifying all pairs of values of the 3D matrix (25) according to the principle of the "Area-under-Curve" (AUC) calculation, (ix) Selecting a pair of values from the set according to step (viii) with the highest AUC value, (x) Checking another pair of values from the set in step (viii), and selecting this pair of values if a limit value for a correlation with the pair of values in step (ix) is smaller than 1.65/N, where N=number of data points or parameter statistics (patients) according to step (vi)

(xi) Repeating step (x) for another pair of values from the set in step (viii), and selecting this pair of values if a limit value for a correlation with the previously selected value pairs is smaller than $1.65\sqrt{N}$ in each case, and (xii) Repeating steps (ix) to (xi) until a predetermined number of e.g. 20 value pairs is reached, which are then defined as specific learning values f and are entered into the AI system (20) for purposes of training.

The above-mentioned steps (v) to (xii) of the further development of the method according to FIG. 9 are each symbolized in simplified form by blocks in the associated flow chart. Here, the arrow "f", which after step (xii) opens out from below into the sequence between steps (iii) and (iv), is understood to mean that the predetermined number of specific learning values f defined in step (xii) are input to the AI system 20 or the neural network $20_N$.

With regard to the advantageous further development of the method according to FIG. 9, it may be pointed out by way of explanation that in step (v) the measured values of the set M of patients 11 are provided in the form of time series, preferably in milliseconds, or in the form of heartbeats. The formation of the 3D matrix 25 in step (vii) is shown symbolically in FIG. 10a. The set M of all patients is plotted as an ordinate and can be divided, e.g. seen from top to bottom, first into a group of healthy patients (e.g. without CHD findings) and then into a group of sick patients (e.g. with CHD findings). The 3D matrix includes the set M of the total 284 time series as well as the scalar personal parameters, which are shown in FIGS. 11a-11d. However, only the 282 time series parameters are included in the training of the neural network.

With respect to the 292 parameters shown in FIGS. 11a, 11b, 11c, and 11d, it is separately noted that there are 284 time series parameters. 8 personal scalar parameters, which refer to a respective screened patient, are considered for the probability calculations using Bayes theorem.

At this point, it is separately noted that in the above method, in steps (x) and (xi) of which, the individual limit values for the respective correlations with the pair of values of step (ix) do not assume a constant fixed value, but instead are each dependent on the number of heartbeats or the majority of time series parameters in step (vi). Thus, higher correlations are allowed for short time series (and thus smaller values of N), and vice versa.

Figure 10A:
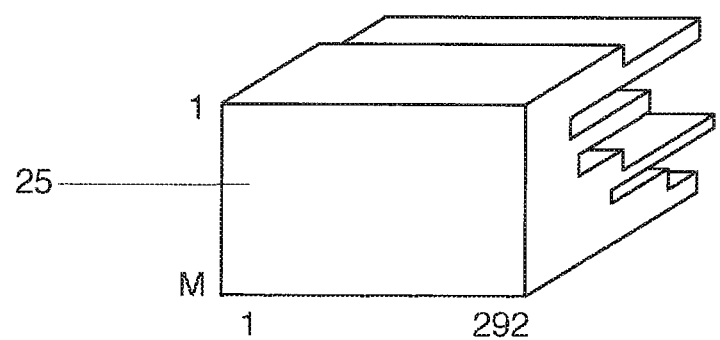
FIG. 10 is a basically simplified representation of a 3D matrix (FIG. 10a) of measured values or a standardized version thereof (FIG. 10b), with the statistics derived from the time series parameter or parameters, which are used in a method according to FIG. 8 or FIG. 9, FIG. 11a-11d show exemplary time series parameters applicable to a method according to FIG. 9.
Figure 10B:
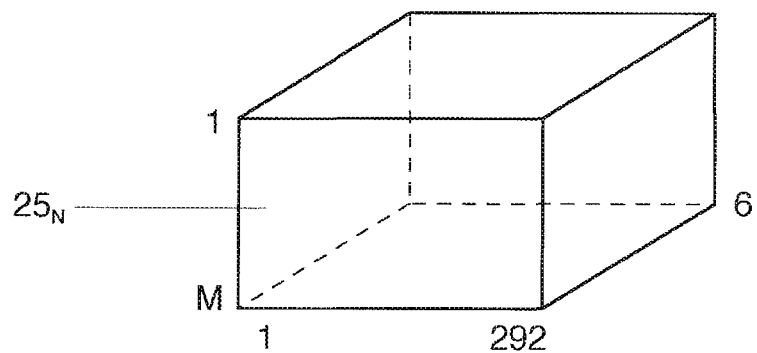

FIG. 10b shows the 3D matrix in a standardized version with uniform depth, which is achieved by linking or offsetting their columns (=patient data) and rows (=time series parameters) with a plurality of statistical methods, six of which are shown as examples in FIG. 12, namely:
 mean value
 variance
 kurtosis,
 skew,
 5% quantile,
 95% quantile.

The possible application of these six methods is indicated by the entry of "6" (in the image area on the right) in the illustration of FIG. 10b. In this connection it is pointed out that in step (vii) at least one of these statistical methods, or even several such methods, can be used to define both the depth of the 3D matrix 25 and, if necessary, to achieve a uniform depth for the realization of a standardized matrix $25_N$.

Furthermore, for the method shown in FIG. 9, it may be pointed out by way of clarification that in step (viii) the AUC calculation can be performed empirically or according to the principle of Johnson distribution. The principle of Johnson distribution is known per se state of the art, but could be used for the first time with the present invention in connection with the evaluation of patient data or ECG signals for the purpose of early detection of the presence of CHD and/or HRD.

As already explained, for evaluating the data for the purpose of creating a diagnosis, it is advantageous if the AI system 20, into which the specific learning values f are input, comprises at least one neural network $20_N$ or a plurality of such networks $20_N$.

By means of the present invention it is possible, as explained, on the one hand to perform a method for early detection of the presence of CHD and/or HRD of a patient 11 to be screened, as is shown and explained in the flow chart of FIG. 8. On the other hand, in order to improve the diagnosis of the patient 11, it is possible to subject the AI system 20 (or a neural network $20_N$) to training before the actual measurement, as shown and explained in the flow chart of FIG. 9. Such training is carried out on the basis of the data of such patients of whom there is a clear knowledge with regard to their state of health ("healthy" or "sick"). In this respect, such training in the sense of the previous invention is also called "supervised learning".

Figure 13:
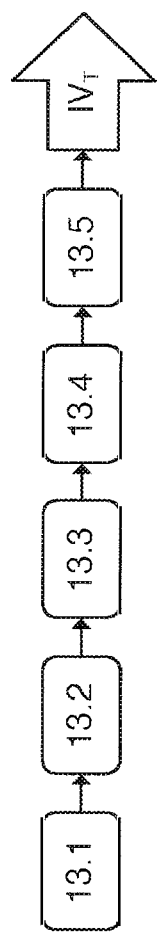
FIG. 13 is a flow chart in which a method according to the present invention is carried out.

These two possibilities, namely both an upstream training for the AI system 20 (or a neural network $20_N$) and the actual performance of the measurement of a patient 11 for the purpose of creating a desired diagnosis, are shown again below in the flow charts of FIG. 13 and FIG. 14. The flow chart of FIG. 13 shows with its blocks 13.1-13.5 a step sequence for the purpose of training the AI system 20. Such training serves to optimize the actual examination or diagnosis of a patient 11, which is carried out by the step sequence of the flow chart in FIG. 14.

In the flow chart of FIG. 13, step 13.1 is substantially the same as step (i) of FIG. 8, with step 13.2 being substantially the same as step (ii) of FIG. 8. The same applies to step 13.3, which essentially corresponds to step (iii) of FIG. 8. To avoid repetition, reference may therefore be made to the explanations of FIG. 8 for these steps 13.1, 13.2 and 13.3.

The following step 13.4 in the flow chart of FIG. 13 corresponds to a parameter extraction, in which—corresponding to steps (v) to (vii) of FIG. 9—time series parameters are combined or offset with the measured values of a set M of patients 11. Here too, it proves to be an advantage if this is done on the basis of spherical coordinates into which the leads A, D, H, I and V are suitably converted.

The following step 13.5 aims at feature evaluation and corresponds essentially to a sequence of steps (viii) to (xii) of FIG. 9, which has already been mentioned and explained above. This means that the specific learning values f are determined or identified using this feature evaluation according to step 13.5.

Subsequently, in the flow chart of FIG. 13, namely in step $IV_T$, the specific learning values f are input into the AI system 20 (or to a neural network $20_N$) in accordance with step (iv) of FIG. 8. As a result, the AI system 20 is suitably trained by the input of the specific learning values f. At this point it should be pointed out again that it is of great advantage in the context of this training that the number of specific learning values f is relatively low and can assume the value 20, for example. Alternatively, the number of specific learning values f may be fewer or greater than 20, and may be, for example, 15 or 25. In any case, with respect to the training of the AI system 20 discussed herein, it is to be understood that these learning values f are always obtained from the data of a patient 11 for whom there is a clear knowledge regarding their state of health ("healthy" or "sick").

Figure 14:
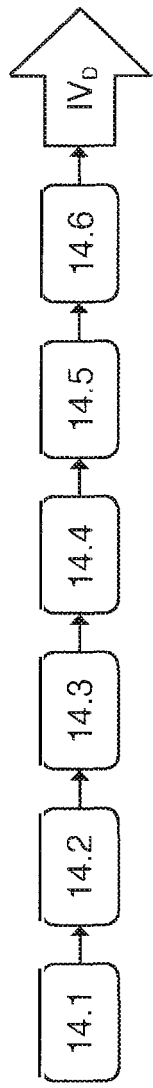
FIG. 14 is a further flow chart in which a method according to the present invention is carried out according to a further embodiment.

The flow chart of FIG. 14 illustrates with its sequence of steps the diagnosis actually carried out for a patient 11. Here, steps 14.1, 14.2 and 14.3 essentially correspond to steps 13.1-13.3, so that, in order to avoid repetition, reference can be made to the explanation of steps 13.1-13.3.

Step 14.5 in the flow chart of FIG. 14 provides a feature selection—here, only the data of a screened patient 11 are used on the basis of those recorded ECG signals that correspond to the specific learning values f previously determined in step 13.5. These selected features or values are then compared with the predetermined specific learning values f in step 14.6 ("trained network"). Subsequently, in step $IV_D$, the actual diagnosis $IV_D$ is made for the patient 11 with the help of the trained AI system 20, in accordance with step (iv) of FIG. 8.

The diagnosis of a patient 11 explained above, performed with a device 10 of FIG. 1 and by a method according to the flow chart of FIG. 8 or FIG. 14, as well as the training of an AI system 20 (or a neural network $20_N$) which is carried out according to the flow chart of FIG. 9 and FIG. 13, respectively, are always based on the fact that the sensors S1-S4 are place on the body of the patient 11, e.g. by using the t-shirt of FIG. 3. Now, according to a further method according to the present invention, it is possible to compensate for a possibly incorrect fit of these sensors S1-S4 on the body of the patient 11, so that a realistic diagnosis for the patient 11 continues to be ensured. Such a method, hereinafter briefly referred to as "correction method", first provides that a space vector 24 (cf. FIG. 7a) related to the heart 12 of the patient 11, which represents the vector of the electrical field generated by the activity of the heart 12, is determined and suitably displayed. Here, measured values of the heart 12 are recorded on the patient's body 14 at a total of four lead points E1-E4, as has already been explained above in connection with FIG. 2. In the case of the aforementioned correction method, based on the leads A, D, H, I and V (cf. FIG. 5a, FIG. 5b), an orthogonal system with the relationships $$x = D \cos 45° - I$$

$$y = D \sin 45° + A$$

$$z = (V-H) \sin 45°$$

is formed, wherein the measured values for the patient 11 and the space vector 24 determined therefrom are mapped to this orthogonal system x, y, z.

Thus, with reference to the illustrations in FIG. 5a, FIG. 5b, FIG. 15 and FIG. 16, the correction method then in particular provides the following steps:

(a) Performing a measurement on a patient using the first to fourth lead points E1-E4 on the patient's body 14 to thereby obtain a cardiogram for that patient, (b) Extracting the amplitudes of the R wave from the cardiogram of step (a) for each heartbeat in the x, y and z direction, (c) Determining mean values µx, µy, µz and standard deviations σx, σy, σz of the respective amplitudes recorded in millivolts from the cardiogram in step (b), wherein a calculation vector 26 is then formed with these mean values µx, µy, µz and standard deviations σx, σy, σz, (d) Forming a matrix of coefficients 28 obtained on the basis of a Principal Component Analysis for measurements in reference patients by using different formats, (e) Multiplying the calculation vector 26 of step (c) by the coefficient matrix 28 of step (d) to form a resulting vector 30 with a total of six main axes $PC_1$-$PC_6$, (f) Extracting the first main axis $PC_1$ and the second main axis $PC_2$ from the resulting vector 30 of step (e) to form a reference point $PC_1$, $PC_2$ in the space of the first and second main axis, (g) Determining a Euclidean distance of the reference point $PC_1$, $PC_2$ from a predetermined target point $PC_1^{fit}$, $PC_2^{fit}$, which corresponds to a correct position of the four lead points E1-E4 on the human body 14, and (h) if the distance of the reference point $PC_1$, $PC_2$ from the predetermined target point $PC_1^{fit}$, $PC_2^{fit}$ is greater than a predetermined maximum value: Performing an angular correction for a first triangle 31 formed by the first lead point E1, the third lead point E3 and the fourth lead point E4, and for a second triangle 32 formed by the first lead point E1, the second lead point E2 and the fourth lead point E4, so that the Euclidean distance between the reference points $PC_1$, $PC_2$ and the predetermined target point $PC_1^{fit}$, $PC_2^{fit}$ is minimized by adapting the orthogonal system x, y, z to the changed geometry.

Figures 15, 16:
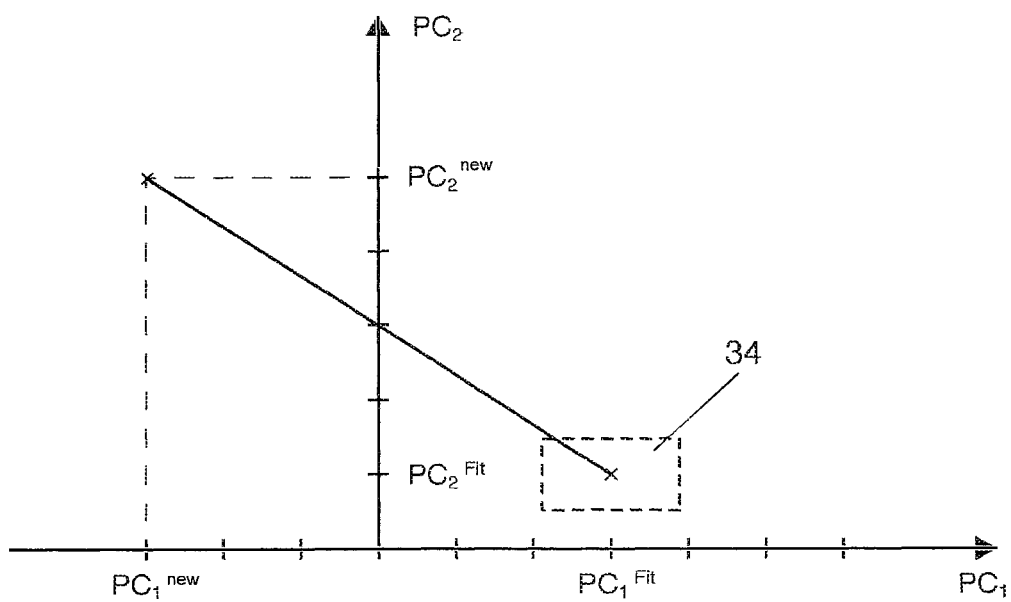
FIG. 15 shows the multiplication of a calculation matrix with a calculation vector according to a further method of the present invention.
FIG. 16 is a basically simplified Principal Component Analysis for the method of FIG. 15.
Figure 17:
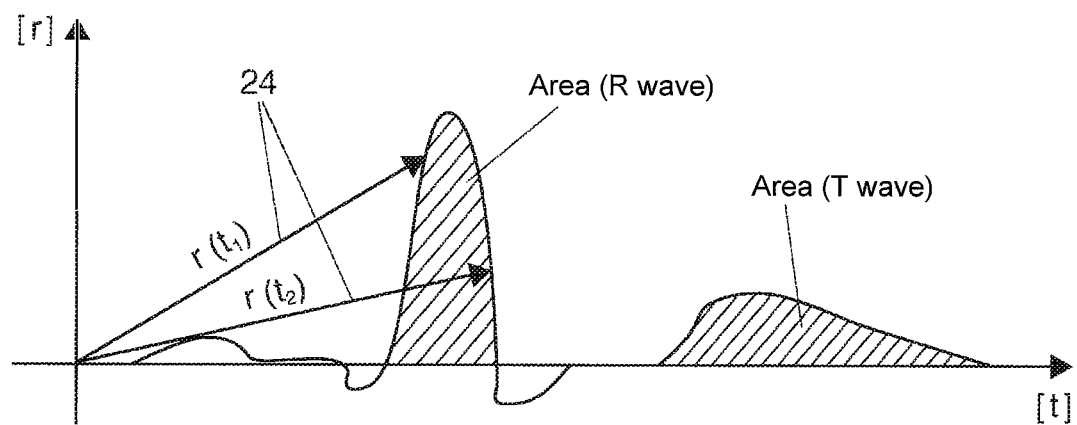
FIG. 17 is a simplified illustration of the formation of a quotient from the areas covered by a length of the space vector (=radius vector) as a function of time during the R wave and during the T wave, respectively.
Figure 18:
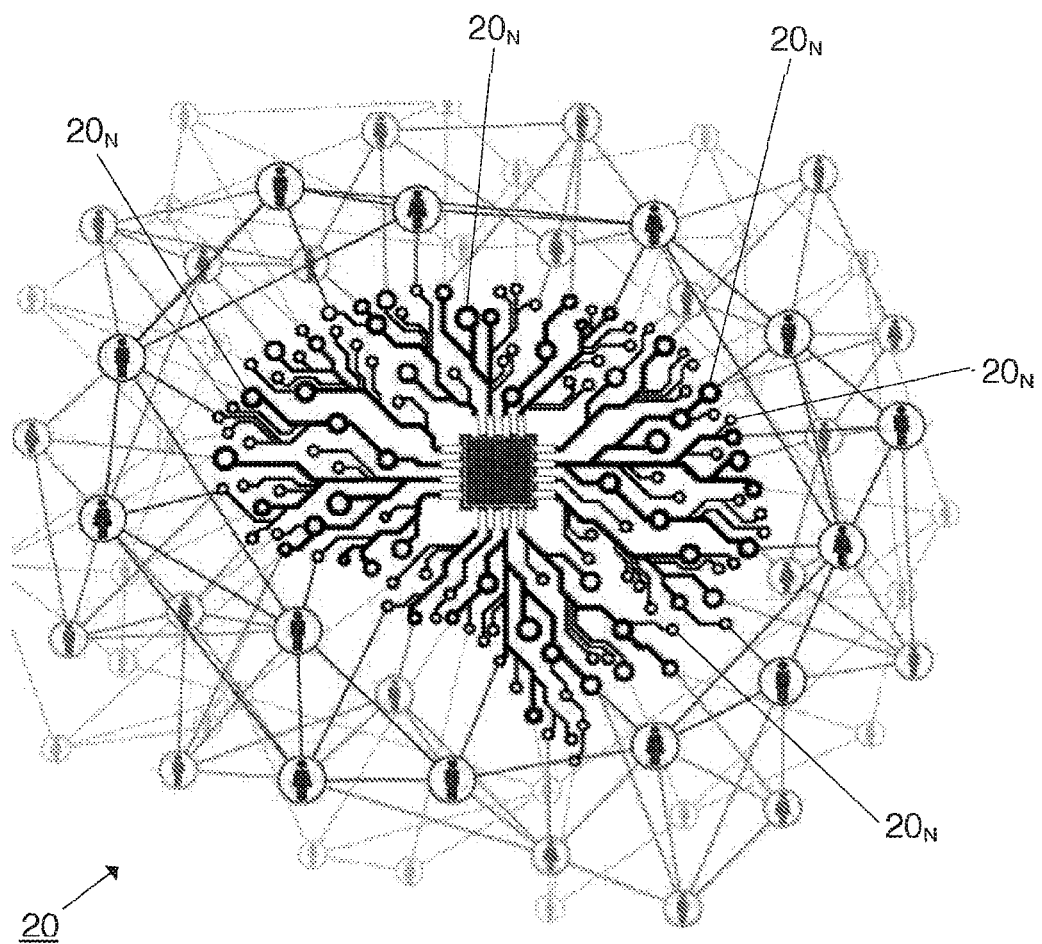
FIG. 18 is a simplified illustration of a plurality of neural networks used in an application or implementation of the present invention.

The above steps (a) to (h) of the correction method are explained as meaning that the amplitudes with which the calculation vector 26 is formed in step (c) are those measured values which were previously measured non-invasively with the ECG signals at the heart 12 of the patient 11 in step (a) or, in the case of the method of FIG. 8, in its step (i), in the case of the method of FIG. 13, in its step 13.1 and/or in the case of the method of FIG. 14, in its step 14.1. Step (e), according to which the calculation vector 26 is multiplied by the 6×6 coefficient matrix 28 of step (d), resulting in the resulting vector 30, is illustrated in FIG. 15. This resulting vector 30 is present in the form of a 6×1 matrix. In step (f), the third to sixth rows of the resulting vector 30, as shown in FIG. 15 marked with the strike-through, are deleted or ignored for the further calculation, wherein the first main axis $PC_1$ and the second main axis $PC_2$ are extracted from the resulting vector 30 to form the reference point $PC_1$, $PC_2$. Furthermore, the Euclidean distance, which is defined in step (g) of the correction method, is illustrated in the diagram of FIG. 16.

The diagram of FIG. 16 also shows an exemplary target area, here symbolized by a rectangle 34 with dashed lines. In this regard, it is noted that prior to performing step (h), the predetermined target point $PC_1^{fit}$, $PC_2^{fit}$ is selected from this target area, which is formed on the basis of standard deviations of a plurality of verified correct measurements of the target point on the human body 14.

In step (h) of the correction method, the angular correction defined herein can be used to determine adjustment values ε, η with which the non-orthogonal angles α of the first triangle 31 and the non-orthogonal angles β of the second triangle 32 can be corrected. Thus it is possible, to compensate for an, in particular, incorrect position of the first lead point E1 at the human body 14 in order to consider, if necessary, any non-orthogonal triangles. In this way, the adjustment value ε represents an adjusted value which, in the case of correctly applied electrodes, is identical to the angle α of the first triangle 31. The same applies to the adjustment value η, which in the case of correctly applied electrodes corresponds to the angle β of the second triangle 32. This relationship is also shown graphically in FIG. 5a and FIG. 5b.

The above adjustment values E, n, which can be used for the angular correction of step (e), can be determined by minimizing the Euclidean distance between reference and target point.

The coefficient matrix 28 by which the calculation vector 26 is multiplied in step (e) is formed by a Principal Component Analysis of a 23×6 matrix based on 23 test measurements and the mean values and standard deviations of the measured values determined therefrom.

The correction method explained above is based on the principle of a Principal Component Analysis, with which, as a result, an incorrect fit of electrodes or sensors S1-S4 on the human body 14 can be compensated. This applies in particular to the position of the sensor S1, which is assigned to first lead point E1, and is advantageous e.g. for the case that the measured values of the heart 12 are acquired with the t-shirt 22 of FIG. 3.

It has already been pointed out above in the discussion of FIG. 7a, that the space vector 24 shown therein, which is determined on the basis of vectorcardiography, represents the electrical activity of the heart 12. For the present invention, this also defines a heart monitoring method in which a quotient of the areas covered by a length of the space vector 24 (=radius vector) as a function of time is calculated during the R wave and during the T wave, respectively, wherein this quotient is then fed to be further evaluated. These areas covered by the space vector 24 as a function of time are shown by way of example in the diagram in FIG. 17.

For the present invention, it has been found that for the screened heart 12 of a patient 11, an ischemia or coronary artery disease (CAD) is detected if the quotient formed by the areas covered by the space vector 24 respectively during the R wave and during the T wave is Area($R$-wave)/Area($T$-wave)=$a$ outside an interval between the limit values $a_{0,CHD}$ and $a_{1,CHD}$.

A special case of the above findings is the case when a cardiac arrhythmia (HRD) is detected for the screened heart 12, if the quotient formed by the areas covered by the space vector 24 during the R wave and during the T wave, respectively, satisfies the condition Area($R$-wave)/Area($T$-wave)=$a_{0,HRD}$ or the condition Area($R$-wave)/Area($T$-wave)=$a_{1,HRD}$ With regard to the limit values $a_{0,CHD}$ and $a_{1,CHD}$ or $a_{0,HRD}$ and $a_{1,HRD}$, with which the quotient formed by the area (R wave)/area (T wave) in the screening for the presence of CHD and/or HRD in the actual examination of a patient is compared or correlated in each case, reference may be made, in order to avoid repetition, to the explanations in the introductory part of the present patent application, according to which these limit values can also be determined or optimized as a function of a training set.

The various findings, which for the latter method according to the present invention, based on the ratio of the areas which are covered by the space vector 24 as a function of time during the R wave and during the T wave, respectively, can of course also be applied or taken into account in the aforementioned methods according to the invention, which are shown and explained by means of the flow charts according to FIG. 8, FIG. 9, FIG. 13 and FIG. 14, respectively.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:
1. A method for early detection of a presence of coronary heart disease (CHD) and/or cardiac arrhythmia (HRD) in a patient to be screened, the method comprising:
   (i) non-invasive recording of ECG signals at the heart of the patient in the resting state;
   (ii) filtering processing of the recorded ECG signals;
   (iii) converting the filtered ECG signals into orthogonalized measured values based on vectorcardiography; and
   (iv) inputting the orthogonalized measured values into a system based on artificial intelligence, in which already known findings data of reference patients is stored, wherein a diagnosis of CHD and/or HRD is made for the screened patient by comparing the entered orthogonalized measured values with the findings data of the reference patients within the AI system;
wherein the AI system is trained prior to step (iv),
wherein the AI system comprises at least one neural network,
wherein, for training the AI system, a number of specific learning values is input therein, the number of specific learning values being between 10 and 30 or the number of specific learning values being 20,
wherein the specific learning values are determined by the following sequence of steps:
   (v) providing measured values of a set (M) of patients with a known finding, wherein these measured values are orthogonalized based on vectorcardiography;
   (vi) providing a plurality of time series parameters and at least one statistical method;
   (vii) forming a 3D matrix, wherein the orthogonalized measured values of the set of patients define the rows, the time series parameters define the columns and the at least one statistical method defines the depth of this matrix;
   (viii) classifying all pairs of values of the 3D matrix according to the principle of the "Area-under-Curve" (AUC) calculation;
   (ix) selecting a pair of values from the set in step (viii) with the highest AUC value;
   (x) checking another pair of values from the set in step (viii), and selecting this pair of values, if a limit value for a correlation with the value pair of step (ix) is smaller than $1.65/\sqrt{N}$, where N=number of the data points or parameter statistics (patients) in step (vi);
   (xi) repeating step (x) for another pair of values from the set in step (viii), and selecting this pair of values if a limit value for a correlation with the previously selected value pairs is in each case smaller than $1.65/\sqrt{N}$; and (xii) repeating the steps (ix) to (xi) until a predetermined number of value pairs is reached, which are then defined as specific learning values for training the AI system.

2. The method according to claim 1, wherein in step (i) the ECG signals are recorded at a total of four lead points on the body of the patient.

3. The method according to claim 2, wherein potential differentials are measured in the form of an anterior lead between a first lead point and a fourth lead point, a dorsal lead between a second lead point and the fourth lead point, a horizontal lead between a third lead point and the fourth lead point, a vertical lead between the first lead point and the third lead point, and an inferior lead between the first lead point and the second lead point.

4. The method according to claim 3, wherein the leads between the respective lead points are converted into spherical coordinates.

5. The method according to claim 2, wherein, for recording the ECG signals a t-shirt is used, which has four sensors assigned to a correct position of the four lead points on the body of the patient.

6. The method according to claim 1, wherein in step (v) the measured values of the set of patients are provided in the form of time series, preferably in milliseconds, or in the form of heartbeats.

7. The method according to claim 1, wherein in step (vi) the at least one statistical method includes a plurality of statistical methods.

8. The method according to claim 7, wherein, after step (vii), a standardized matrix is calculated from the data of the 3D matrix using at least one statistical method of the plurality of statistical methods, thus achieving a uniform depth.

9. The method according to claim 7, wherein the plurality of statistical methods includes mean value, variance, kurtosis, skew, 5% quantile, and 95% quantile.

10. The method according to claim 1, wherein in step (viii) the AUC calculation is performed empirically or according to the principle of Johnson distribution.

* * * * *